(12) United States Patent
Caldirola et al.

(10) Patent No.: US 6,399,617 B1
(45) Date of Patent: Jun. 4, 2002

(54) USE

(75) Inventors: Patrizia Caldirola; Sukhwinder Jossan, both of Uppsala; Kjell S. Sakariassen, Hasselby; Jan Svartengren, Uppsala, all of (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 09/908,798

(22) Filed: Jul. 20, 2001

Related U.S. Application Data

(60) Provisional application No. 60/222,284, filed on Aug. 1, 2000.

(30) Foreign Application Priority Data

Jul. 21, 2000 (SE) ................................. 0002739

(51) Int. Cl.$^7$ ..................... A61K 31/495; A61K 31/505
(52) U.S. Cl. ............................ 514/253.05; 514/253.06; 514/256; 514/275
(58) Field of Search ................ 514/253.05, 253.06, 514/256, 275, 363, 373, 395

(56) References Cited

U.S. PATENT DOCUMENTS

| | | | |
|---|---|---|---|
| 5,968,817 A | * | 10/1999 | Sutcliffe et al. |
| 6,030,976 A | * | 2/2000 | Bos et al. |
| 6,060,642 A | * | 5/2000 | Tecott et al. |
| 6,316,450 B1 | * | 11/2001 | Bromidge et al. |

FOREIGN PATENT DOCUMENTS

| | | |
|---|---|---|
| EP | 0 611 003 A1 | 8/1994 |
| EP | 0 815 861 A1 | 1/1998 |
| EP | 1 072 597 A1 | 1/2001 |
| JP | 11-171856 | 6/1999 |
| WO | WO 98/27081 | 6/1998 |
| WO | WO 98/29411 | 7/1998 |
| WO | WO 99/02502 | 1/1999 |
| WO | WO 99/42465 | 8/1999 |

OTHER PUBLICATIONS

Li et al., 5HT(1A) receptor antagonists enhance. . . , Database Embase, AN:1998058304, abstract, Brain research, Jan. 19, 1998, vol. 781/1–2, pp. 121–128.*

Lemberger et al., Use of specific serotonin uptake inhibitors as antidepressants, Database Embase, AN 86074399., abstract, Clinical neuropharmacology, 1985, vol. 8/4, pp. 299–317.*

* cited by examiner

Primary Examiner—William R. A. Jarvis
Assistant Examiner—Vickie Kim
(74) Attorney, Agent, or Firm—Fish & Richardson P.C.

(57) ABSTRACT

The invention provides a method of treatment or prophylaxis of obesity, comprising administering to a patient in need of such treatment a therapeutically effective amount of an aryl sulfonamide compound of formula (I) or formula (II)

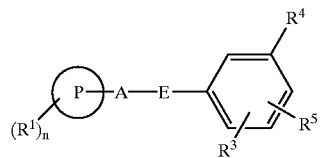

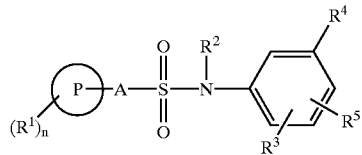

wherein the substituents are as described in the specification.

11 Claims, 1 Drawing Sheet

USE

This application claims benefit of 60/222,284 filed Aug. 1, 2000.

TECHNICAL FIELD

The present invention relates to the use of aryl sulfonamide compounds, active as 5-HT$_6$ receptor antagonists, in the treatment of obesity.

BACKGROUND ART

Obesity is a condition characterized in an increase in body fat content resulting in excess body weight above accepted norms. Obesity is the most important nutritional disorder in the western world and represents a major health problem in all industrialized countries. This disorder leads to increased mortality due to increased incidences of diseases such as cardiovascular disease, digestive disease, respiratory disease, cancer and NIDDM (type II diabetes). Searching for compounds, which reduce body weight has been going on for many decades. One line of research has been activation of serotonergic systems, either by direct activation of serotonin receptor subtypes or by inhibiting serotonin reuptake. The exact receptor subtype profile required is however not known.

Serotonin (5-hydroxytryptamine or 5-HT), a key transmitter of the peripheral and central nervous system, modulate a wide range of physiological and pathological functions, including anxiety, sleep regulation, aggression, feeding and depression. Multiple serotonin receptor subtypes have been identified and cloned. One of these, the 5-HT$_6$ receptor, was cloned by several groups in 1993 (M Ruat, E Traiffort, J-M Arrang, J Tardivel-Lacombe, J Diaz, R Leurs, J-C Shwartz. *Biochem. Biophys. Res. Commun.* 1993, 193 (1) 268–276; M Sebben, H Ansanay, J Bockaert, A Dumuis, *NeuroReport* 5, 2553–2557 (1994).) This receptor is positively coupled to adenylyl cyclase and displays affinity for antidepressants such as clozapine. Recently, the effect of 5-HT$_6$ antagonist and 5-HT$_6$ antisense oligonucleotides to reduce food intake in rats has been reported (J C Bentley, C A Mardsen, A J Sleight and K C Fone Effect of 5-HT$_6$ antagonist Ro 04-6790 on food consumption in rats traineds to a fixed feeding regime *Br J Pharmac.* 1999 Suppl 126 P66; J C Bentley, A J Sleight, C A Mardsen, K C F Fone 5-HT$_6$ antisense oligonucleotide ICV affects rat performance in the water maze and feeding *J Psychopharmacol Suppl A*64 1997 255).

Aryl sulfonamide compounds have been disclosed as possessing 5-HT$_6$ receptor activity and being useful in the treatment of CNS disorders (EP 815861). Further classes of aryl sulfonamide compounds with 5-HT$_6$ receptor activity have been reported in WO 98/27081 and WO 99/42465. The compounds are believed to be of potential use in the treatment of certain CNS disorders.

The object of the present invention is to present an improved method of treatment of obesity. A further object is a new use of compounds for the manufacture of medicaments for obesity treatment.

Figure 1:
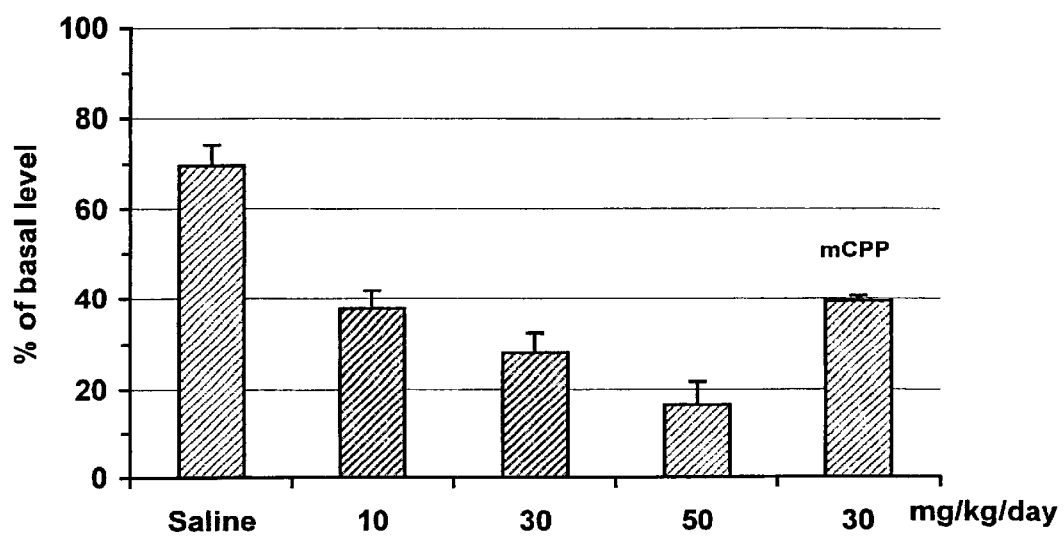
FIG. 1

Effect of SB-271046 (5-Chloro-3-methyl-benzo-[b]thiophene-2-sulphonic acid (4-methoxy-3-piperazin-yl-phenyl)-amide monohydrochloride) on food intake in ob/ob mice. mCPP (m-chloro-phenylpiperazine) was used as a positive control.

SUMMARY OF THE INVENTION

The objects of the invention are achieved by the method of treatment and use of the compounds as claimed in the claims. According to the invention a method of treatment or prophylaxis of obesity in mammals including humans is provided. The method comprises administering to a patient in need of such treatment a therapeutically effective amount of a compound of formula (I) or formula (II)

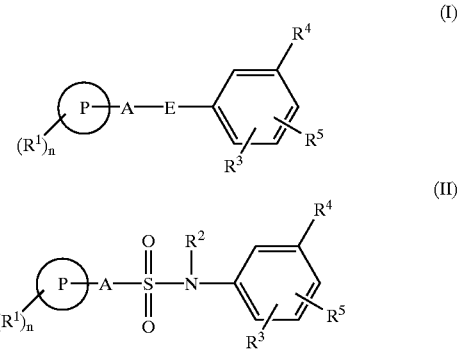

wherein

E is —SO$_2$NH— or —NHSO$_2$—;

R$^2$ is hydrogen, C$_{1-6}$ alkyl or arylC$_{1-6}$alkyl;

P is phenyl, naphthyl a bicyclic heterocyclic ring or is a 5- to 7-membered heterocyclic ring each containing 1 to 4 heteroatoms selected from oxygen, nitrogen or sulfur;

A is a single bond, a C$_{1-6}$ alkylene or a C$_{1-6}$ alkenylene group;

R$^1$ is halogen, C$_{1-6}$ alkyl, optionally substituted by one or more halogen atoms, C$_{3-6}$ cycloalkyl, COC$_{1-6}$ alkyl, C$_{1-6}$ alkoxy, OCF$_3$, hydroxy, hydroxy C$_{1-6}$alkyl, hydroxy C$_{1-6}$alkoxy, C$_{1-6}$ alkoxy C$_{1-6}$ alkoxy, C$_{1-6}$ alkanoyl, acyl, nitro, amino, alkylamino or dialkylamino, cyano or SR$^{11}$ where R$^{11}$ is hydrogen or C$_{1-6}$ alkyl or R$^1$ is phenyl, benzyl, naphthyl, a bicyclic heterocyclic ring, or is a 5 to 7-membered heterocyclic ring, each containing 1 to 4 heteroatoms selected from oxygen, nitrogen or sulfur;

n is 0, 1, 2, 3, 4, 5 or 6;

R$^3$ is a group R$^5$ or together with R$^5$ forms a group (CH$_2$)$_2$O or (CH$_2$)$_3$O or R$^3$ is linked to R$^2$ to form a group (CH$_2$)$_2$ or (CH$_2$)$_3$;

R$^4$ is —X(CH$_2$)p-R$^6$ wherein
X is a single bond, CH$_2$, O, NH or N—C$_{1-6}$-alkyl;
p is 0 to 6 and
R$^6$ is an optionally substituted 5- to 7-membered heterocyclic ring containing 1 to 3 heteroatoms selected from nitrogen, sulfur or oxygen, or R$^6$ is NR$^7$R$^8$ wherein R$^7$ and R$^8$ are independently hydrogen, C$_{1-6}$ alkyl or aryl C$_{1-6}$ alkyl, or R$^4$ is selected from a group of formula (i), (ii) or (iii)

Formula (i)

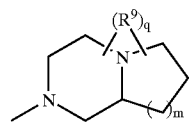

wherein $R^9$ is $C_{1-6}$alkyl, or $C_{1-6}$alkyl substituted by one or more halogen atoms;

m is 0, 1 or 2;

q is 0, 1, 2, 3 or 4; or

Formula (ii)

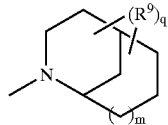

wherein $R^6$, m and q are as defined in formula (i); or

Formula (iii)

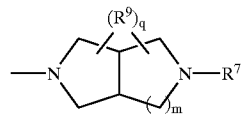

wherein $R^9$, m and q are as defined in formula (i) and $R^7$ is hydrogen or $C_{1-6}$alkyl;

$R^5$ is hydrogen, halogen, $C_{1-6}$alkyl, $C_{1-6}$alkoxy, optionally substituted with one or more fluorine atoms, $C_{3-6}$ cycloalkyl, $COC_{1-6}$ alkyl, $C_{1-6}$ alkoxy, hydroxy, hydroxy $C_{1-6}$alkyl, hydroxy $C_{1-6}$alkoxy, $C_{1-6}$alkoxy$C_{1-6}$alkoxy, acyl, nitro, trifluoromethyl or together with $R^3$ forms a group $(CH_2)_2O$ or $(CH_2)_3O$, cyano or aryl.

Preferably, in formula (I):

$R^1$ is halogen, $C_{1-6}$ alkyl, optionally substituted by one or more fluorine atoms, $C_{3-6}$ cycloalkyl, $C_{1-6}$ alkoxy, $OCF_3$, $C_{1-6}$ alkoxy $C_{1-6}$ alkoxy, $C_{1-6}$ alkanoyl, amino, alkylamino or dialkylamino, $SR^{11}$ where $R^{11}$ is hydrogen or $C_{1-6}$ alkyl or $R^1$ is phenyl, benzyl, naphthyl, a bicyclic heterocyclic ring, or is a 5 to 7-membered heterocyclic ring, each containing 1 to 4 heteroatoms selected from oxygen, nitrogen or sulfur;

n is 0, 1, 2, 3, 4 or 5;

$R^3$ is a group $R^5$ or together with $R^5$ forms a group $(CH_2)_2O$ or $(CH_2)_3O$;

$R^4$ is selected from a group of formula (i), (ii) or (iii) as mentioned above;

$R^5$ is hydrogen, halogen, $C_{1-6}$alkyl, $C_{1-6}$alkoxy, optionally substituted with one or more fluorine atoms, trifluoromethyl or together with $R^3$ forms a group $(CH_2)_2O$ or $(CH_2)_3O$.

Preferably, in formula (II):

$R^1$ is halogen, $C_{1-6}$alkyl optionally substituted by one or more halogen atoms, $C_{3-6}$ cycloalkyl, $COC_{1-6}$ alkyl, $C_{1-6}$alkoxy, $OCF_3$, hydroxy, hydroxy $C_{1-6}$alkyl, hydroxy $C_{1-6}$alkoxy, $C_{1-6}$alkoxy$C_{1-6}$alkoxy, acyl, nitro, amino, alkylamino or dialkylamino, cyano or $R^1$ is phenyl, naphthyl, a bicyclic heterocyclic ring or is a 5 to 7-membered heterocyclic ring, each containing 1 to 4 heteroatoms selected from oxygen, nitrogen or sulfur;

$R^4$ is $-X(CH_2)p-R^6$ where X is a single bond, $CH_2$, O, NH or N—$C_{1-6}$-alkyl and p is 0 to 6 and $R^6$ is an optionally substituted 5- to 7-membered heterocyclic ring containing 1 to 3 heteroatoms selected from nitrogen, sulfur or oxygen, or $R^6$ is $NR^7R^8$ where $R^7$ and $R^8$ are independently hydrogen, $C_{1-6}$ alkyl or aryl $C_{1-6}$ alkyl and $R^5$ is hydrogen, halogen, $C_{1-6}$ alkyl, $C_{3-6}$ cycloalkyl, $COC_{1-6}$ alkyl, $C_{1-6}$ alkoxy, hydroxy, hydroxy $C_{1-6}$alkyl, hydroxy $C_{1-6}$alkoxy, $C_{1-6}$alkoxy$C_{1-6}$alkoxy, acyl, nitro, trifluoromethyl, cyano or aryl.

The compounds of formula (I) and (II) can also be used in the form of pharmaceutically acceptable salts thereof.

DETAILED DESCRIPTION OF THE INVENTION

According to the present invention, it has surprisingly been found that 5-$HT_6$ receptor antagonists, belonging to the aryl sulfonamide compounds disclosed in WO 98/27081 and WO 99/42465, reduce food intake and body weight. An improved method of treating obesity is therefore provided by the present invention.

In the formulas the alkyl groups may be straight chained or branched both alone and as part of another group. Preferred alkyl groups are methyl and ethyl. "Halogen" means a group selected from fluorine, chlorine, bromine or iodine.

When the group P is a bicyclic heterocyclic ring suitable examples include benzothienyl, indolyl, quinolinyl or isoquinolinyl. When P is a 5 to 7- membered heterocyclic ring suitable examples include thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl, pyrrolidinyl and pyrazinyl. The heterocyclic rings can be linked to the remaining molecule via any suitable carbon atom or, when present, a nitrogen.

Preferably P is phenyl, naphthyl, thienyl and most preferably benzothienyl. Suitably A is a single bond, a methylene or ethylene group or a —CH=CH— group. Preferably A is a single bond or methylene.

Preferably $R^1$ is halogen, or $C_{1-6}$ alkyl optionally substituted by one or more halogen atoms, for example methyl or trifluoromethyl. When $R^1$ is a heterocyclic group suitable examples include those listed above for P. Preferably n is 0, 1, 2 or 3, particularly 1 or 2.

Suitably $R^2$ is hydrogen or $C_{1-6}$ alkyl. Preferably $R^2$ is hydrogen.

It will be appreciated that when $R^3/R^5$ groups are linked together the two groups must be attached to adjacent carbon atoms of the phenyl ring. Preferably $R^3$ is a group $R^5$, in particular hydrogen.

In formula (I) $R^4$ is preferably a group:

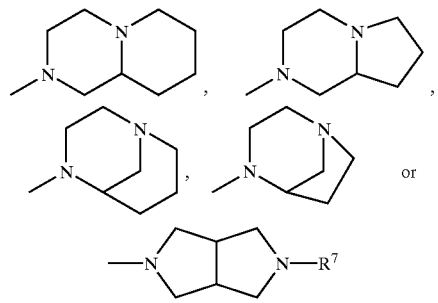

Preferably $R^5$ is $C_{1-6}$ alkoxy, most preferably methoxy. Preferably $R^5$ is para with respect to the sulfonamide linkage.

In formula (II) $R^4$ is preferably meta with respect to the sulfonamide linkage. Preferably X is a bond, p is 0 and $R^6$ is an optionally substituted 5- to 7-membered heterocyclic ring. The heterocyclic rings can be linked to the remaining molecule via a carbon atom or, when present, a nitrogen atom. Optional substituents for these rings, which can be present on carbon and/or nitrogen atoms, include $C_{1-6}$ alkyl, in particular methyl. More preferably $R^4$ is N-piperazine optionally substituted by $C_{1-6}$ alkyl, particularly unsubstituted piperazine.

A preferred meaning for P-A is benzo[b]thiophen-2yl or benzo[b]thiophen-3-yl optionally substituted by one or two $R^1$ groups, especially 5-chloro-3-methyl-benzo[2]thiophen-2-yl.

A particularly preferred compound of the invention is 5-chloro-N-(4-methoxy-3-piperazin-1-yl-phenyl)-3-methyl-2-benzothiophenesulfonamide.

The compounds of the formula (I) and (II) can form acid addition salts with acids such as conventional pharmaceutically acceptable acids, for example maleic, hydrochloric, hydrobromic, phosphoric, acetic, fumaric, salicylic, citric, lactic, mandelic, tartaric and methanesulfonic.

Compounds of formula (I) and (II) may also form solvates such as hydrates and the invention also extends to these forms. When referred to herein, it is understood that the term "compound of formula (I) and (II)" also includes these forms.

Certain compounds of formula (I) and (II) are capable of existing in stereoisomeric forms including diastereomers and enantiomers and the invention extends to each of these stereoisomeric forms and to mixtures thereof including racemates. The different stereoisomeric forms may be separated one from the other by the usual methods. Any given isomer may be obtained by stereospecific or asymmetric synthesis. The invention also extends to any tautomeric forms and mixtures thereof.

The compounds used in the invention are prepared according to the methods described in WO 98/27081 and WO 99/42465 the contents of which are hereby included by reference.

According to the present invention the compounds for obesity treatment can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15$^{th}$ Ed., 1975). The compounds and compositions can be administered orally, parenterally (for example, by intravenous, intraperitoneal or intramuscular injection), topically, or rectally. Preferably the compounds are administered orally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously, or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound can be administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may be presented in a single dose or as divided doses administered at appropriate intervals. The compositions can be administered orally, sublingually, transdermally, or parenterally at dose levels of about 0.01 to about 150 mg/kg, preferably about 0.1 to about 50 mg/kg, and more preferably about 0.1 to about 30 mg/kg of mammal body weight.

EXAMPLE

Effect of Compounds on Food Intake in ob/ob Mice

Animals

Obese (ob/ob) mouse is selected as the primary animal model for screening as this mutant mouse consumes high amounts of food resulting in a high signal to noise ratio. To further substantiate and compare efficacy data, the effect of the compounds on food consumption is also studied in wild type (C57BL/6J) mice. The amount of food consumed during 15 hours of infusion of compounds is recorded.

Male mice (obese C57BL/6JBom-Lep$^{ob}$ and lean wild-type C57B1/6JBom; Bomholtsgaard, Denmark) 8–9 weeks with an average body weight of 50 g (obese) and 25 g (lean) are used in all the studies. The animals are housed singly in cages at 23±1° C., 40–60% humidity and have free access to water and standard laboratory chow. The 12/12-h light/dark cycle is set to lights off at 5 p.m. The animals are conditioned for at least one week before start of study.

Compounds

The test compounds are dissolved in solvents suitable for each specific compound such as cyclodextrin, cyclodextrin/methane sulfonic acid, polyethylene glycol/methane sulfonic acid, or saline. Fresh solutions are made for each study. Doses of 30, 50 and 100 mg kg$^{-1}$day$^{-1}$ are used. The purity of the test compounds is of analytical grade.

Minipump implantation

The animals are weighed at the start of the study and randomized based on body weight. Alzet osmotic minipumps (Model 2001D; infusion rate 8 μl/h) are used and loaded essentially as recommended by the Alzet technical information manual (Alza Scientific Products, 1997; Teeuwes and Yam, 1976). Continuous subcutaneous infusion with 24 hours duration is used. The minipumps are either filled with different concentrations of test compounds dissolved in vehicle or with only vehicle solution and maintained in vehicle pre-warmed to 37° C. (approx. 1 h). The minipumps are implanted subcutaneously in the neck/back region under short acting anesthesia (metofane/enflurane). This surgical procedure lasts approximately 5 min. It takes about 3 h to reach steady state delivery of the compound.

Food intake measurements

The weights of the food pellets are measured at 5 p.m. and at 8 p.m. for two days before (baseline) and one day after the implantation of the osmotic minipumps. The weighing is performed with a computer assisted Mettler Toledo PR 5002 balance. Occasional spillage is corrected for. At the end of the study the animals are killed by neck dislocation and trunk blood sampled for later analysis of plasma drug concentrations.

Determination of plasma concentration

The plasma sample proteins are precipitated with methanol, centrifuged and the supernatant is transferred to HPLC vials and injected into the liquid chromatography/mass spectrometric system. The mass spectrometer is set for electrospray positive ion mode and Multiple Reaction Monitoring (MRM with the transition m/z 316⇌221).

A linear regression analysis of the standards forced through the origin is used to calculate the concentrations of the unknown samples.

Statistical evaluation

Food consumption for 15 hours is measured for the three consecutive days and the percentage of basal level values is derived for each animal from the day before and after treatment. The values are expressed as mean±SD and mean±SEM from eight animals per dose group. Statistical evaluation is performed by Kruskal-Wallis one-way ANOVA using the per cent basal values. If statistical significance is reached at the level of p<0.05, Mann-Whitney U-test for statistical comparison between control and treatment groups is performed.

Results

FIG. 1 shows the reduction of food intake, after subcutaneous continuos infusion of test compound SB-271046 (5-Chloro-3-methyl-benzo-[b]thiophene-2-sulphonic acid (4-methoxy-3-piperazin-yl-phenyl)-amide monohydrochloride) at the dose of 10, 30 and 50 mg/kg/day. The compound induced significant reduction of food intake of 45% (0.006*), 60% (0.019*) and 77% (0.034*) respectively compared to the basal level of food intake. *Free plasma concentration at the steady state giving the effect at the respective doses. m-Chloro-phenylpiperazine (mCPP) was used as a positive control.

What is claimed is:

1. Method of treatment or prophylaxis of obesity in mammals, comprising administering to a patient in need of such treatment a therapeutically effective amount of a compound of formula (I) or formula (II)

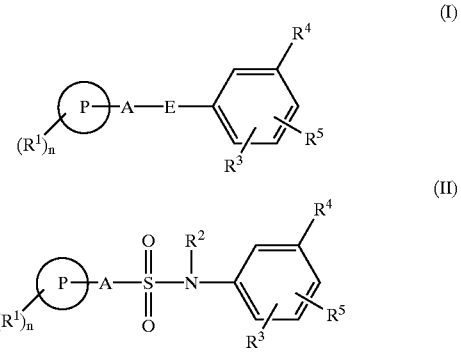

wherein

E is —$SO_2NH$— or —$NHSO_2$—;

$R^2$ is hydrogen, $C_{1-6}$ alkyl or aryl$C_{1-6}$alkyl;

P is phenyl, naphthyl a bicyclic heterocyclic ring or is a 5- to 7-membered hererocyclic ring each containing 1 to 4 heteroatoms selected from oxygen, nitrogen and sulfur;

A is a single bond, a $C_{1-6}$ alkylene or a $C_{1-6}$ alkenylene group;

$R^1$ is halogen, $C_{1-6}$ alkyl, optionally substituted by one or more halogen atoms, $C_{3-6}$ cycloalkyl, $COC_{1-6}$ alkyl, $C_{1-6}$ alkoxy, $OCF_3$, hydroxy, hydroxy $C_{1-6}$alkyl, hydroxy $C_{1-6}$alkoxy, $C_{1-6}$ alkoxy $C_{1-6}$ alkoxy, $C_{1-6}$ alkanoyl, acyl, nitro, amino, alkylamino or dialkylamino, cyano or $SR^{11}$ where $R^{11}$ is hydrogen or $C_{1-6}$ alkyl or $R^1$ is phenyl, benzyl, naphthyl, a bicyclic heterocyclic ring, or is a 5 to 7-membered heterocyclic ring, each containing 1 to 4 heteroatoms selected from oxygen, nitrogen and sulfur;

n is 0, 1, 2, 3, 4, 5 or 6;

$R^3$ is a group $R^5$ or together with $R^5$ forms a group $(CH_2)_2O$ or $(CH_2)_3O$ or $R^3$ is linked to $R^2$ to form a group $(CH_2)_2$ or $(CH_2)_3$;

$R^4$ is —$X(CH_2)p$-$R^6$ where X is a single bond, $CH_2$, O, NH or N—$C_{1-6}$-alkyl and p is 0 to 6 and $R^6$ is an optionally substituted 5- to 7-membered heterocyclic ring containing 1 to 3 heteroatoms selected from nitrogen, sulfur and oxygen, or $R^6$ is $NR^7R^8$ where $R^7$ and $R^8$ are independently hydrogen, $C_{1-6}$ alkyl or aryl $C_{1-6}$ alkyl, or $R^4$ is selected from a group of formula (i), (ii) and (iii)

Formula (i)

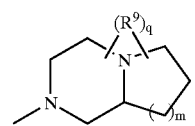

wherein $R^9$ is $C_{1-6}$alkyl, or $C_{1-6}$alkyl substituted by one or more halogen atoms;

m is 0, 1 or 2;

q is 0, 1, 2, 3 or 4; or

Formula (ii)

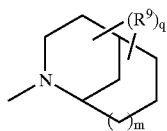

wherein $R^9$, m and q are as defined in formula (i); or
Formula (iii)

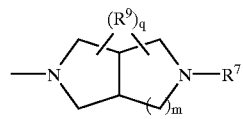

wherein $R^9$, m and q are as defined in formula (i) and $R^7$ is hydrogen or $C_{1-6}$alkyl;

$R^5$ is hydrogen, halogen, $C_{1-6}$alkyl, $C_{1-6}$alkoxy, optionally substituted with one or more fluorine atoms, $C_{3-6}$ cycloalkyl, $COC_{1-6}$ alkyl, $C_{1-6}$ alkoxy, hydroxy, hydroxy $C_{1-6}$alkyl, hydroxy $C_{1-6}$alkoxy, $C_{1-6}$alkoxy$C_{1-6}$alkoxy, acyl, nitro, trifluoromethyl or together with $R^3$ forms a group $(CH_2)_2O$ or $(CH_2)_3O$, cyano or aryl;

or pharmaceutically acceptable salts thereof.

2. The method according to claim 1 wherein:

$R^1$ is halogen, $C_{1-6}$ alkyl, optionally substituted by one or more fluorine atoms, $C_{3-6}$ cycloalkyl, $C_{1-6}$ alkoxy, $OCF_3$, $C_{1-6}$ alkoxy $C_{1-6}$ alkoxy, $C_{1-6}$ alkanoyl, amino, alkylamino or dialkylamino, $SR^{11}$ where $R^{11}$ is hydrogen or $C_{1-6}$ alkyl or $R^1$ is phenyl, benzyl, naphthyl, a bicyclic heterocyclic ring, or is a 5 to 7-membered heterocyclic ring, each containing 1 to 4 heteroatoms selected from oxygen, nitrogen and sulfur;

n is 0, 1, 2, 3, 4 or 5;

$R^3$ is a group $R^5$ or together with $R^5$ forms a group $(CH_2)_2O$ or $(CH_2)_3O$;

$R^4$ is selected from a group of formula (i), (ii) and (iii) as mentioned above;

$R^5$ is hydrogen, halogen, $C_{1-6}$alkyl, $C_{1-6}$alkoxy, optionally substituted with one or more fluorine atoms, trifluoromethyl or together with $R^3$ forms a group $(CH_2)_2O$ or $(CH_2)_3O$ in formula (I).

3. The method according to claim 1 wherein:

$R^1$ is halogen, $C_{1-6}$alkyl optionally substituted by one or more halogen atoms, $C_{3-6}$ cycloalkyl, $COC_{1-6}$ alkyl, $C_{1-6}$alkoxy, $OCF_3$, hydroxy, hydroxy $C_{1-6}$alkyl, hydroxy $C_{1-6}$alkoxy, $C_{1-6}$alkoxy$C_{1-6}$alkoxy, acyl, nitro, amino, alkylamino or dialkylamino, cyano or $R^1$ is phenyl, naphthyl, a bicyclic heterocyclic ring or is a 5 to 7-membered heterocyclic ring, each containing 1 to 4 heteroatoms selected from oxygen, nitrogen and sulfur;

$R^4$ is —$X(CH_2)p-R^6$ where X is a single bond, $CH_2$, O, NH or N—$C_{1-6}$-alkyl and p is 0 to 6 and $R^6$ is an optionally substituted 5- to 7-membered heterocyclic ring containing 1 to 3 heteroatoms selected from nitrogen, sulfur and oxygen, or $R^6$ is $NR^7R^8$ where $R^7$ and $R^8$ are independently hydrogen, $C_{1-6}$ alkyl or aryl $C_{1-6}$ alkyl and $R^5$ is hydrogen, halogen, $C_{1-6}$ alkyl, $C_{3-6}$ cycloalkyl, $COC_{1-6}$ alkyl, $C_{1-6}$ alkoxy, hydroxy, hydroxy $C_{1-6}$alkyl, hydroxy $C_{1-6}$alkoxy, $C_{1-6}$alkoxy$C_{1-6}$alkoxy, acyl, nitro, trifluoromethyl, cyano or aryl in formula (II).

4. The method according to any of claims 1 to 3, wherein P is benzothienyl.

5. The method according to claim 1 wherein $R^1$ is halogen or $C_{1-6}$ alkyl optionally substituted with one or more halogen atoms.

6. The method according to claim 1 wherein $R^2$ is hydrogen.

7. The method according to claim 1 wherein $R^4$ in formula (II) is an unsubstituted piperazine ring.

8. The method according to claim 1 wherein $R^5$ is $C_{1-6}$ alkoxy.

9. The method according to claim 1 wherein P—A is 5-chloro-3-methyl-benzo[2]thiophen-2-yl.

10. The method according to claim 1 wherein the compound is 5-chloro-N-(4-methoxy-3-piperazin-1-yl-phenyl)-3-methyl-2-benzothiophenesulfonamide.

11. The method according to claim 1, wherein the mammals are humans.

* * * * *

UNITED STATES PATENT AND TRADEMARK OFFICE
CERTIFICATE OF CORRECTION

PATENT NO. : 6,399,617 B1  Page 1 of 1
DATED : June 4, 2002
INVENTOR(S) : Patrizia Calirola et al.

It is certified that error appears in the above-identified patent and that said Letters Patent is hereby corrected as shown below:

Title page,
Item [57], ABSTRACT,
Lines 6-19, 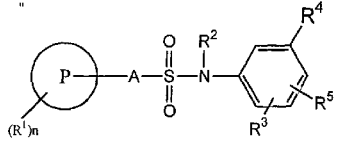 should read 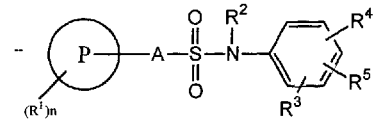

Column 1,
Line 43, delete "traineds" and insert -- trained --

Column 2,
Lines 17 through 24, 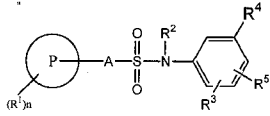 should read 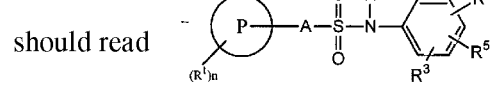

Column 6,
Line 32, delete "0.   1" and insert -- 0.1 --

Column 7,
Line 33, delete "316⇔221" and insert -- 316⇒221 --

Column 8,
Lines 10 through 16, 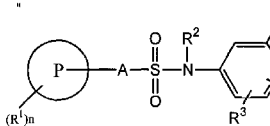 should read 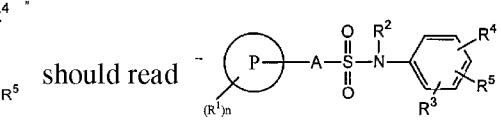

Line 22, delete "hereocyclic" and insert -- heterocyclic --

Signed and Sealed this

Ninth Day of September, 2003

JAMES E. ROGAN
*Director of the United States Patent and Trademark Office*